US012773149B2

(12) United States Patent
Zhou et al.

(10) Patent No.: US 12,773,149 B2
(45) Date of Patent: Oct. 27, 2026

(54) PHYSIOLOGICAL SIGNAL ACQUISITION DEVICES AND WEARABLE DEVICES

(71) Applicant: SHENZHEN SHOKZ CO., LTD., Shenzhen (CN)

(72) Inventors: Xin Zhou, Shenzhen (CN); Lei Su, Shenzhen (CN); Meiqi Li, Shenzhen (CN); Yuxiang Zhang, Shenzhen (CN); Jia Liu, Shenzhen (CN); Fengyun Liao, Shenzhen (CN); Xin Qi, Shenzhen (CN)

(73) Assignee: SHENZHEN SHOKZ CO., LTD., Shenzhen (CN)

( * ) Notice: Subject to any disclaimer, the term of this patent is extended or adjusted under 35 U.S.C. 154(b) by 167 days.

(21) Appl. No.: 18/757,413

(22) Filed: Jun. 27, 2024

(65) Prior Publication Data

US 2024/0341655 A1 Oct. 17, 2024

Related U.S. Application Data

(63) Continuation of application No. PCT/CN2022/107594, filed on Jul. 25, 2022.

(51) Int. Cl.

| | |
|---|---|
| *A61B 5/296* | (2021.01) |
| *A61B 5/25* | (2021.01) |
| *A61B 5/27* | (2021.01) |

(52) U.S. Cl.

CPC ................ *A61B 5/296* (2021.01); *A61B 5/27* (2021.01); *A61B 2560/0468* (2013.01); *A61B 2562/16* (2013.01)

(58) Field of Classification Search

CPC ... A61B 5/296; A61B 5/27; A61B 2560/0468; A61B 2562/16

See application file for complete search history.

(56) References Cited

U.S. PATENT DOCUMENTS 11,019,734 B1 * 5/2021 Davis .................... A61B 5/053
2003/0176908 A1 9/2003 Lin (Continued)

FOREIGN PATENT DOCUMENTS

CN 202699125 U 1/2013
CN 104970788 A 10/2015

(Continued)

OTHER PUBLICATIONS

International Search Report in PCT/CN2022/107594 mailed on Apr. 24, 2023, 7 pages.

(Continued)

*Primary Examiner* — Adam Z Minchella
(74) *Attorney, Agent, or Firm* — METIS IP LLC

(57) ABSTRACT

Disclosed is a physiological signal acquisition device. The physiological signal acquisition device may include a first insulating membrane, first absorbent members, and at least two electrodes. At least two first guide grooves may be arranged in a first direction on the first insulating membrane, and the at least two first guide grooves may be insulated from each other. The first absorbent members may be arranged in the at least two first guide grooves and configured to absorb moisture. The at least two electrodes may be configured to contact a skin and acquire physiological signals, wherein the at least two electrodes may cover the at least two first guide grooves and may be attached to surfaces of the first absorbent members near the skin.

20 Claims, 5 Drawing Sheets

300

(56) References Cited

U.S. PATENT DOCUMENTS

| | | | | |
|---|---|---|---|---|
| 2013/0172722 | A1 | 7/2013 | Ninane et al. | |
| 2014/0005515 | A1* | 1/2014 | Huang ................... | A61B 5/388 600/386 |
| 2014/0039292 | A1 | 2/2014 | Su et al. | |
| 2016/0278702 | A1* | 9/2016 | Chen ......................... | A61B 5/24 |
| 2020/0046246 | A1 | 2/2020 | Shu et al. | |
| 2022/0183151 | A1 | 6/2022 | Katsu et al. | |
| 2024/0341655 | A1 | 10/2024 | Zhou et al. | |

FOREIGN PATENT DOCUMENTS

| | | | |
|---|---|---|---|
| CN | 106214148 | A | 12/2016 |
| CN | 112774024 | A | 5/2021 |
| CN | 214965704 | U | 12/2021 |
| CN | 215961794 | U | 3/2022 |
| EP | 2684516 | A1 | 1/2014 |
| EP | 2695575 | A1 | 2/2014 |
| JP | 3177243 | U | 7/2012 |
| TW | I536961 | B | 6/2016 |
| WO | 2006082384 | A2 | 8/2006 |

OTHER PUBLICATIONS

Written Opinion in PCT/CN2022/107594 mailed on Apr. 24, 2023, 6 pages.

* cited by examiner

PHYSIOLOGICAL SIGNAL ACQUISITION DEVICES AND WEARABLE DEVICES

CROSS-REFERENCE TO RELATED APPLICATIONS

This application is a Continuation of International Application No. PCT/CN2022/107594, filed on Jul. 25, 2022, the content of which is hereby incorporated by reference.

TECHNICAL FIELD

The present disclosure relates to the field of physiological signal acquisition, and in particular, to physiological signal acquisition devices and wearable devices.

BACKGROUND

When acquiring physiological signals during human physical activity, sweat produced by the body may cause abnormal electrode connections, resulting in signal attenuation and inaccuracy. Therefore, it is desirable to propose a physiological signal acquisition device that can accurately acquire physiological signals even in moist, humid, or water-infiltrated environments.

SUMMARY

One or more embodiments of the present disclosure provide a physiological signal acquisition device. The physiological signal acquisition device may include a first insulating membrane, first absorbent members, and at least two electrodes. At least two first guide grooves may be arranged in a first direction on the first insulating membrane, and the at least two first guide grooves may be insulated from each other. The first absorbent members may be configured to absorb moisture, and the first absorbent members may be arranged in the at least two first guide grooves. The at least two electrodes may be configured to contact a skin and acquire physiological signals. The at least two electrodes may cover the at least two first guide grooves and may be attached to surfaces of the first absorbent members near the skin.

In some embodiments, the physiological signal acquisition device may further include at least one second guide groove arranged in the first direction. Each of the at least one second guide groove may be positioned between two adjacent first guide grooves of the at least two first guide grooves, and a second absorbent member may be arranged in the at least one second guide groove.

In some embodiments, a material of the second absorbent member may be the same as a material of the first absorbent members.

In some embodiments, the physiological signal acquisition device may further include an insulating water-conducting layer configured to guide moisture on a surface of the skin to a side away from the skin. The insulating water-conducting layer may cover the at least one second guide groove and may be attached to a surface of the second absorbent member near the skin.

In some embodiments, the insulating water-conducting layer in each of the at least one second guide groove may not contact a side wall of the second guide groove.

In some embodiments, a cross-section of a side wall of each of the at least two first guide grooves perpendicular to a third direction may be approximately Y-shaped, and the third direction may be perpendicular to a plane of the first direction and a second direction.

In some embodiments, the first insulating membrane may be a grid structure.

In some embodiments, the physiological signal acquisition device may further include a second insulating membrane. The second insulating membrane may be positioned on a side of the physiological signal acquisition device away from the skin.

In some embodiments, the second insulating membrane may be a grid structure.

In some embodiments, a material of the first insulating membrane or a material of the second insulating membrane may include at least one of rubber, polymer, or silicone.

In some embodiments, the physiological signal acquisition device may further include modified fabric configured to prevent absorbed moisture from conducting transversally in the first direction. The modified fabric may be positioned on a side of the physiological signal acquisition device away from the skin.

In some embodiments, the at least two electrodes may include conductive fabric electrodes, and the at least two electrodes may allow the moisture to penetrate and be absorbed by the first absorbent members.

In some embodiments, a material of the first absorbent members may include sponge or quick-drying material.

In some embodiments, the first direction may be parallel to a surface of the skin.

In some embodiments, the physiological signal acquisition device may further include an anti-slip strip arranged on a first side of the physiological signal acquisition device. The first side is a side of the physiological signal acquisition device along the first direction, and the anti-slip strip may be configured to prevent slipping and prevent the moisture from flowing in the first direction.

In some embodiments, the physiological signal acquisition device may further include a channel arranged on a second side of the physiological signal acquisition device. The second side is a side of the physiological signal acquisition device along a third direction, and the channel may be configured to guide the moisture to flow in the first direction.

One or more embodiments of the present disclosure provide a wearable device, the wearable device including the physiological signal acquisition device described in any embodiment of the present disclosure.

In some embodiments of the present disclosure, through the structural design and material selection of the physiological signal acquisition device, the physiological signal acquisition device is configured to prevent electrical conduction between electrodes even in the presence of sweat or water, thereby enhancing the accuracy of the physiological signal acquisition device in acquiring and measuring physiological signals.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
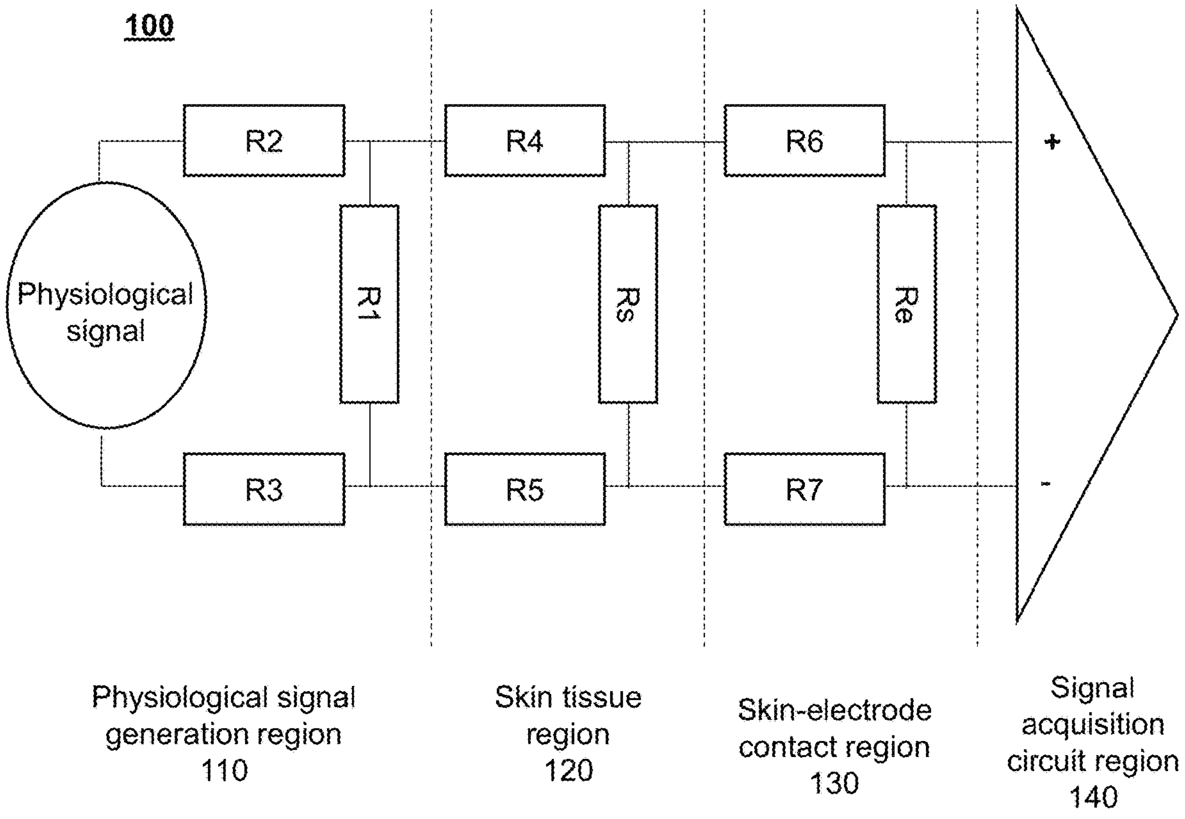
FIG. 1 is a schematic diagram illustrating a principle of a physiological signal acquisition device model according to some embodiments of the present disclosure.

In order to more clearly illustrate the technical solutions of the embodiments of the present disclosure, the accompanying drawings to be used in the description of the embodiments will be briefly described below. Obviously, the accompanying drawings in the following description are only some examples or embodiments of the present disclosure, and that the present disclosure may be applied to other similar scenarios in accordance with these drawings without creative labor for those of ordinary skill in the art. Unless obviously acquired from the context or the context illustrates otherwise, the same numeral in the drawings refers to the same structure or operation.

It should be understood that "system," "device," "unit," and/or "module" as used herein is a way to distinguish between different components, elements, parts, sections, or assemblies at different levels. However, these words may be replaced by other expressions if they accomplish the same purpose.

As indicated in the present disclosure and in the claims, the singular forms "a," "an," and "the" may be intended to include the plural forms as well, unless the context clearly indicates otherwise. In general, the terms "comprise," "comprises," and/or "comprising," "include," "includes," and/or "including," when used in this disclosure, specify the presence of stated features, integers, steps, operations, elements, and/or components, but do not preclude the presence or addition of one or more other features, integers, steps, operations, elements, components, and/or groups thereof.

Flowcharts are used in the present disclosure to illustrate the operations performed by the system according to some embodiments of the present disclosure. It should be understood that the operations described herein are not necessarily executed in a specific order. Instead, the operations may be executed in reverse order or simultaneously. Additionally, one or more other operations may be added to these processes, or one or more operations may be removed from these processes.

One or more embodiments of the present disclosure provide a physiological signal acquisition device. The physiological signal acquisition device may include a first insulating membrane, first absorbent members, and at least two electrodes. At least two first guide grooves may be arranged in a first direction on the first insulating membrane, and the at least two first guide grooves may be insulated from each other. The first absorbent members may be configured to absorb moisture, and the first absorbent members may be arranged in the at least two first guide grooves. The at least two electrodes may be configured to contact a skin and acquire physiological signals. The at least two electrodes may cover the at least two first guide grooves and may be attached to surfaces of the first absorbent members near the skin. Based on the aforementioned structure, the physiological signal acquisition device channels and absorbs sweat produced during physical activity, preventing electrical conduction between electrodes due to the sweat, thereby avoiding signal attenuation and inaccuracies, and ensuring accurate acquisition of physiological signals during the physical activity. The physiological signal acquisition device may be attached to a wearable device through manners such as adhesive bonding, buckling, Velcro, sewing, pressing, or the like, and then secured to a surface of a skin to collect physiological signals via electrodes.

FIG. 1 is a schematic diagram illustrating a principle of a physiological signal acquisition device model according to some embodiments of the present disclosure. As shown in FIG. 1, in a physiological signal acquisition scenario, a physiological signal acquisition model 100 may include a physiological signal generation region 110, a skin tissue region 120, a skin-electrode contact region 130, and a signal acquisition circuit region 140.

The physiological signal generation region 110 refers to a region consist of the human dermis layer and tissues beneath the dermis layer. For example, the physiological signal generation region 110 may include tissues such as fat and muscle. During the physical activity, the tissues may produce physiological signals. The physiological signals may include electromyography (EMG) signals, surface electromyography signals, or the like. In some embodiments, as shown in FIG. 1, the physiological signal generation region 110 may include an impedance R2, an impedance R3, and an impedance R1. The impedance R2 and the impedance R3 are perpendicular to a surface of a skin. The impedance R1 is parallel to the surface of the skin. The impedance R2 and the impedance R3 are related to a thickness of the fat and dermis layers, while the impedance R1 is related to a distance between two electrodes. In some embodiments, if the distance between electrodes remains constant, the larger the thickness of the fat is, the larger the impedance R2 and the impedance R3 become. According to the voltage divider effect, if the impedances become larger, the physiological signal entering the skin tissue region 120 is reduced.

The skin tissue region 120 refers to a region consists of tissues of the human epidermis layer. For example, the skin tissue region 120 may include tissues such as the stratum corneum. In some embodiments, the skin tissue region 120 may include an impedance R4, an impedance R5, and an impedance Rs. The impedance R4 and the impedance R5 are perpendicular to the surface of the skin. The impedance Rs is parallel to the surface of the skin. The impedance R4 and the impedance R5 are related to a thickness of the stratum corneum. The impedance Rs is related to the distance between electrodes. Since the thickness of the stratum corneum is much smaller than the distance between two electrodes, the impedance R4 and the impedance R5 may be considered negligible, and the voltage divider effect may be ignored. However, when sweat or other moisture causes a water film to form between the electrodes on the skin, the impedance Rs may decrease abnormally, thereby reducing the voltage division across the impedance Rs. In this case, the voltage division effect of the impedance R4 and the impedance R5 become significant, and a strength of collected physiological signals decreases correspondingly.

The skin-electrode contact region 130 refers to a region consists of tissues and components where the surface of the skin contacts electrodes. For example, the skin-electrode contact region 130 may include a region consists of hair, sweat, other impurities, air, and electrodes. In some embodiments, the skin-electrode contact region 130 may include an impedance R6, an impedance R7, and impedance Re. The impedance R6 and the impedance R7 are perpendicular to the surface of the skin. The impedance Re is parallel to the surface of the skin. The impedance R6 and the impedance R7 are contact impedances between the skin and the electrodes, while the impedance Re is an impedance between the electrodes. When sweat or other moisture causes a conductive path to form between two electrodes, the impedance Re may decrease abnormally, thereby reducing the voltage division across Re, and significantly lowering the strength of the collected physiological signals. Thus, it impossible to collect the physiological signal.

Figure 2:
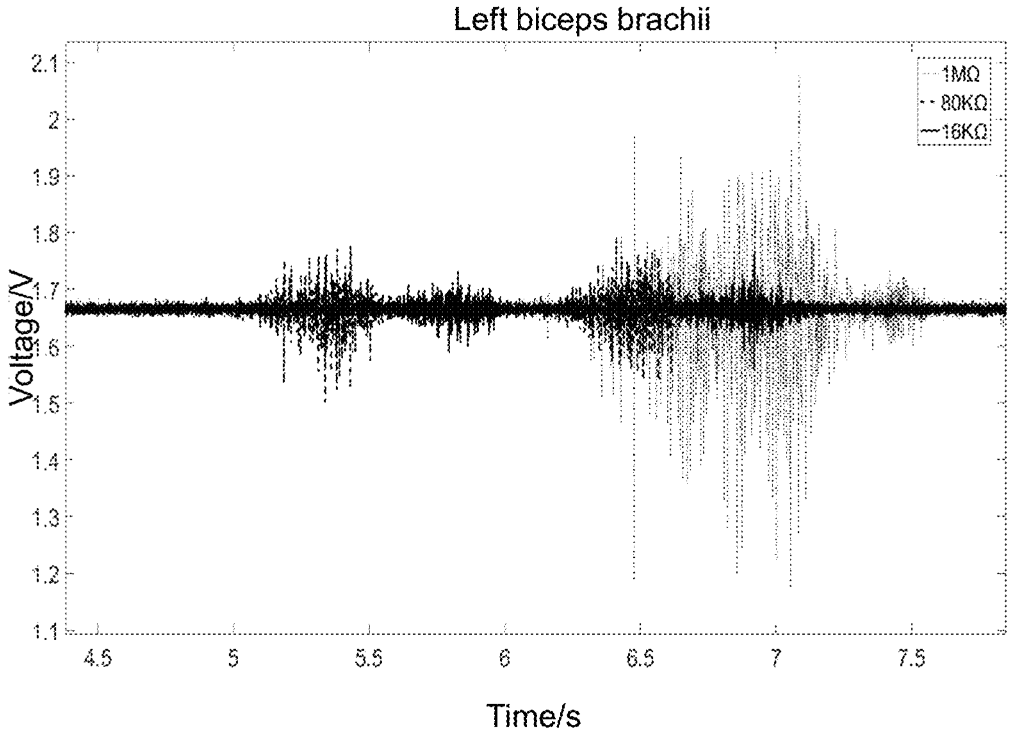
FIG. 2 is a schematic diagram illustrating a comparison between collected physiological signals when impedances between electrodes are different according to some embodiments of the present disclosure.

FIG. 2 is a schematic diagram illustrating a comparison between collected physiological signals when impedances between electrodes are different, according to some embodiments of the present disclosure. As shown in FIG. 2, electromyography (EMG) signals were collected from the left biceps brachii using electrodes with different impedances. When the impedances between the electrodes was 1 MΩ, 80 kΩ, and 16 kΩ, respectively, the collected EMG signals decreased as the impedance between the electrodes decreased. Therefore, conduction between two electrodes may affect the acquisition of the physiological signals.

The signal acquisition circuit region 140 refers to a region consists of components that collect and process physiological signals. For example, the signal acquisition circuit region 140 may include components such as a differential amplifier, a high-pass filter, a low-pass filter, a controller, or the like. In some embodiments, the signal acquisition circuit region 140 processes the collected EMG signals and generates parameters that reflect the physiological signals.

Figure 3A:
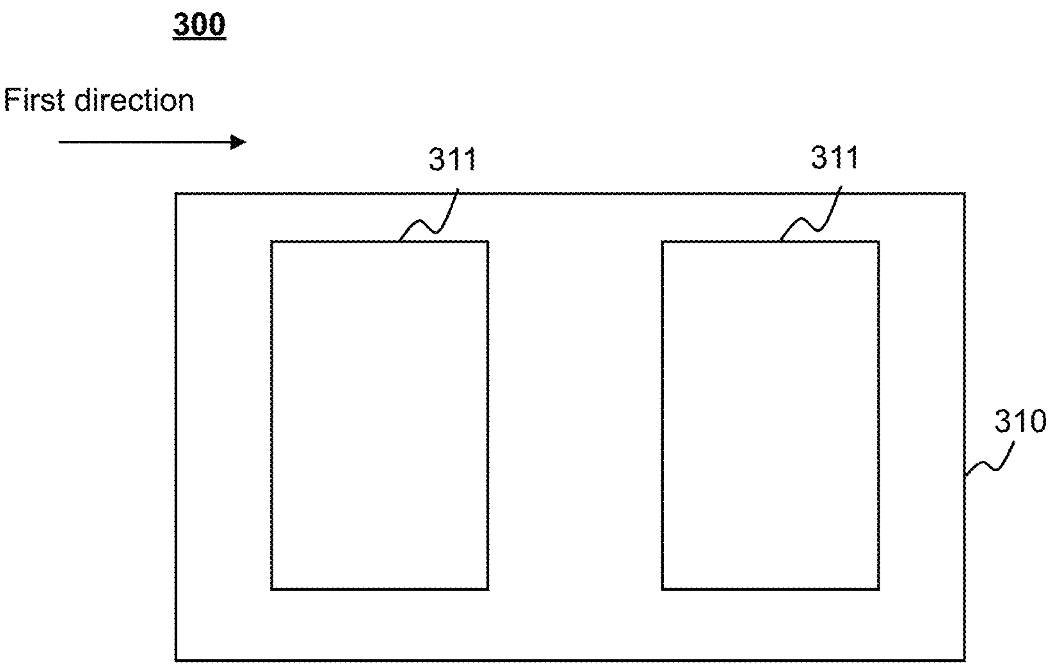
FIG. 3A is a schematic diagram illustrating a top view of an exemplary physiological signal acquisition device according to some embodiments of the present disclosure.
Figure 3B:
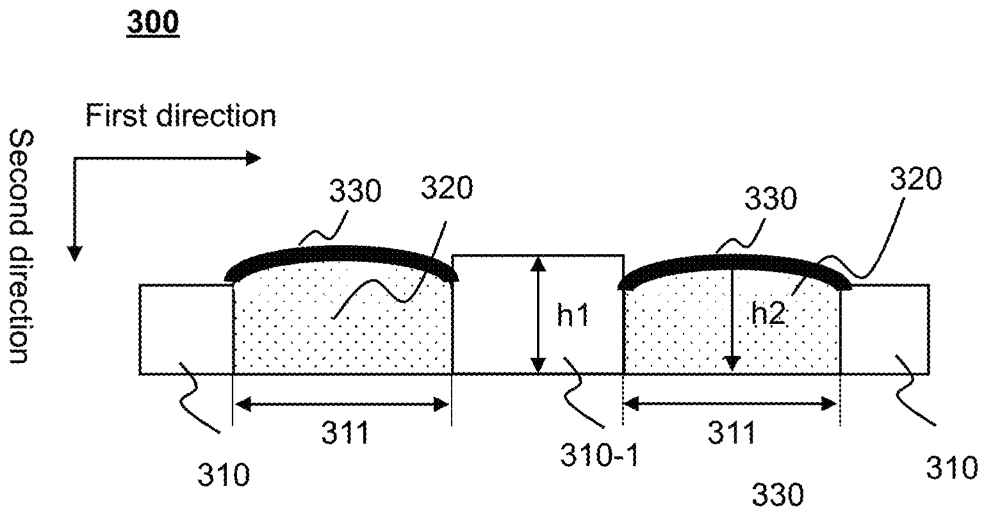
FIG. 3B is a schematic diagram illustrating a cross-sectional view of the exemplary physiological signal acquisition device along a plane perpendicular to a third direction according to some embodiments of the present disclosure.

FIG. 3A is a schematic diagram illustrating a top view of an exemplary physiological signal acquisition device according to some embodiments of the present disclosure. FIG. 3B is a schematic diagram illustrating a cross-sectional view of the exemplary physiological signal acquisition device along a plane perpendicular to a third direction according to some embodiments of the present disclosure.

In some embodiments, a first direction may be parallel to a surface of a skin in contact with a physiological signal acquisition device 300. For example, for the physiological signal acquisition device 300 configured to collect EMG signals, the first direction may be an extension direction of measured muscle fibers. In some embodiments, a second direction may be perpendicular to the surface of the skin. For example, the second direction is perpendicular to the first direction. A plane of a third direction and the first direction may be parallel to the surface of the skin in contact with the physiological signal acquisition device 300, with the third direction being perpendicular to the first direction. For example, for the physiological signal acquisition device 300 configured to collect EMG signals, the third direction may be perpendicular to the extension direction of the measured muscle fibers.

As shown in FIG. 3A and FIG. 3B, the physiological signal acquisition device 300 may include a first insulating membrane 310, first absorbent members 320, and at least two electrodes 330. In some embodiments, at least two first guide grooves 311 may be arranged in the first direction on the first insulating membrane 310, and the at least two first guide grooves 311 may be insulated from each other.

In some embodiments, the first absorbent members 320 may be arranged in the at least two first guide grooves 311, and the first absorbent members 320 may be configured to absorb moisture. In some embodiments, the at least two electrodes 330 may cover the at least two first guide grooves 311 and may be attached to surfaces of the first absorbent members 320 near the skin. The at least two electrodes 330 may be configured to contact the skin of a user and collect physiological signals. In some embodiments, the physiological signals may reflect muscle movement. For example, the physiological signals may include electromyography (EMG) signals, surface EMG signals, or the like. For simplicity of description, the present disclosure takes two first guide grooves 311 and two electrodes 330 as an example for illustration. It should be understood that a count of the at least two first guide grooves 311 and a count of the at least two electrodes 330 may be any number greater than 2, which is not limited by the present disclosure.

In some embodiments, the first insulating membrane 310 may be an insulating piece made of an insulating and waterproof material. The insulating piece may be configured to form the at least two first guide grooves 311 that are insulated from each other, thereby allowing each first guide groove 311 to contain one electrode 330, and preventing electrical conduction between the at least two electrodes 330. In some embodiments, a material of the first insulating membrane 310 may include rubber, polymer, silicone, or the like, or any combination thereof. In some embodiments, to improve breathability and softness of the physiological signal acquisition device 300, the first insulating membrane 310 may be a grid structure. Holes of each grid in the grid structure may extend in the second direction. In some embodiments, the second direction may be perpendicular to the surface of the skin. For example, the second direction is perpendicular to the first direction. For example, the grid structure of the first insulating membrane 310 may include evenly distributed grids, with the holes of each gird extending in the second direction. The grid structure is breathable, and the softness thereof is increased. Moisture (e.g., sweat) flows through the grid structure in the second direction, thereby preventing the moisture from flowing in the first direction and forming a conductive path between the at least two electrodes 330.

The at least two first guide groove 311 may be grooves configured to accommodate the first absorbent members 320 and/or the at least two electrodes 330. The first absorbent members 320 may be components configured to absorb moisture. In some embodiments, a material of the first absorbent members may include sponge or quick-drying material. Examples of the quick-drying material may include polyester fiber, water-absorbing modified polyester fiber, polypropylene fiber, Coolmax fiber, Mony-Dry, or the like, or any combination thereof. In some embodiments, the first absorbent members 320 may be arranged in the at least two first guide grooves 311, and configured to absorb moisture and further direct the moisture to flow along the second direction. In some embodiments, the first absorbent member 320 in each first guide groove 311 may directly contact one electrode 330 of the at least two electrodes 330. When the at least two electrodes 330 contact the skin to collect the user's physiological signals, the first absorbent members 320 may provide a pressure to the at least two electrodes 330, ensuring close contact between the at least two electrodes 330 and the skin. In some embodiments, the first absorbent members 320 may also have water absorption and moisture storage functions. After absorbing the moisture (e.g., sweat from the surface of the skin), the moist first absorbent members 320 may continuously provide the moisture to the at least two electrodes 330, ensuring good conductivity between the at least two electrodes 330 and the skin, thereby improving connectivity of the physiological signal acquisition device 300 with the skin. In some embodiments, the first absorbent members 320 may also have water absorption and quick-drying functions. When there is excess moisture, the first absorbent members 320 may absorb and evaporate the moisture to prevent a formation of a conductive path between the at least two electrodes 330 due to excessive moisture.

The at least two electrodes 330 may be components configured to acquire the physiological signals. For example, when the physiological signal acquisition device 300 collects electromyographic signals, due to different muscle contraction strengths at various muscle positions, the at least two electrodes 330 located in different muscle positions may detect different potentials, resulting in a potential difference between the at least two electrodes 330. The potential difference may be configured to generate parameters representing the physiological signals. In some embodiments, a material of the at least two electrodes 330 may be a material with good conductivity, such as copper, graphite, or the like. In some embodiments, to ensure good contact with the skin, good conductivity, and good breathability, the at least two electrodes 330 may include conductive fabric electrodes. In some embodiments, the at least two electrodes 330 may cover the at least two first guide grooves 311 and attached to the surfaces of the first absorbent members 320 near the skin. When the conductive fabric electrodes (e.g., the at least two electrodes 330) contact the skin, the conductive fabric electrodes allow the moisture to penetrate and be absorbed by the first absorbent members 320. In some embodiments, the conductive fabric electrodes may include a plurality of micro-holes to retain a small amount of moisture to enhance an electrical contact between the at least two electrodes 330 and the skin. The plurality of micro-holes may retain excess moisture passes through the micro-holes into the first absorbent members 320 and absorbed by the first absorbent members 320. In some embodiments, the at least two electrodes 330 may be connected to a terminal device via a data interface to transmit the collected physiological signals to the terminal device. Examples of the terminal device may include a medical device, a computer, a mobile phone, a wearable device, or the like.

In some embodiments, to prevent excessive moisture and the formation of a conductive path between the at least two electrodes 330 on the surface in contact with the skin, a thickness of the first insulating membrane 310 located between any two adjacent electrodes among the at least two electrodes 330 may be greater than or equal to a sum of a thickness of the electrodes and a thickness of the first absorbent members 320 in each of the at least two first guide grooves 311. In the present disclosure, the thickness of the first insulating membrane 310, the thickness of the electrodes 330, and the thickness of the first absorbent members 320 refers to a length of the first insulating membrane 310, a length of the electrodes 330, and a length of the first absorbent members 320 in the second direction, respectively. For example, as shown in FIG. 3B, the thickness h1 of the first insulating membrane 310-1 between any two adjacent electrodes among the at least two electrodes 330 may be greater than or equal to a sum h2 of a thickness of an electrode and a thickness of a first absorbent member 320 in each of the at least two first guide grooves 311. In some embodiments, to prevent the formation of the conductive path between the at least two electrodes 330 on the surface in contact with the skin, the first insulating membrane 310 may also be configured as other structures, for example, a first insulating membrane 410 illustrated in FIG. 4B.

Through the physiological signal acquisition device described in some embodiments of the present disclosure, by draining and absorbing sweat generated during the human activity, the physiological signal acquisition device prevents electrical conduction between electrodes due to sweat conductivity, thereby avoiding abnormal reduction or misalignment of the physiological signals, and achieving accurate acquisition of the physiological signals during the human activity.

Figure 4A:
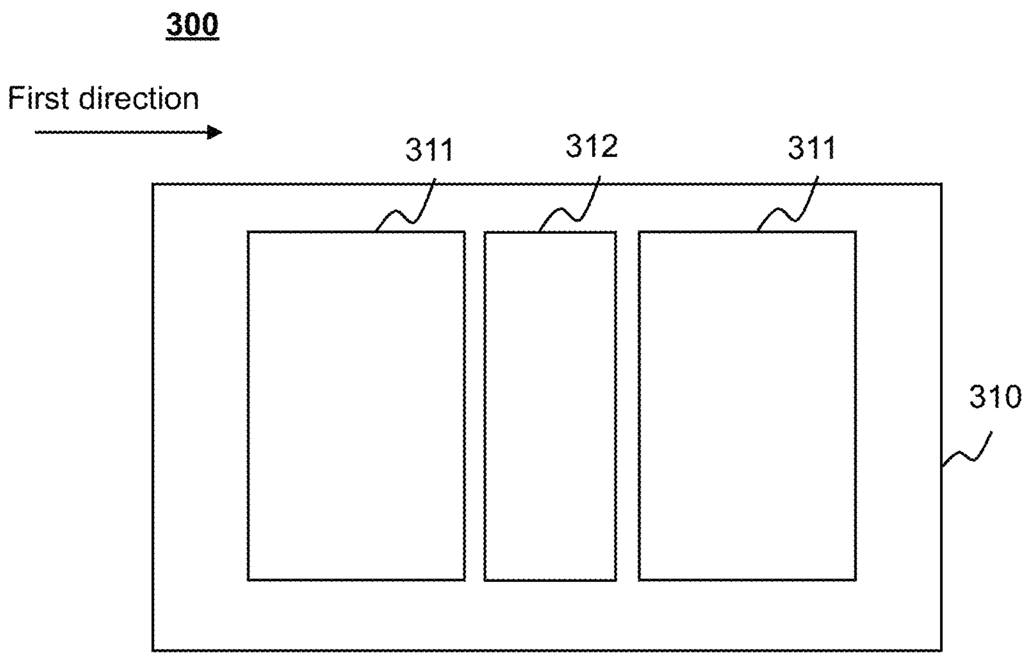
FIG. 4A is a schematic diagram illustrating a top view of an exemplary physiological signal acquisition device according to some embodiments of the present disclosure.
Figure 4B:
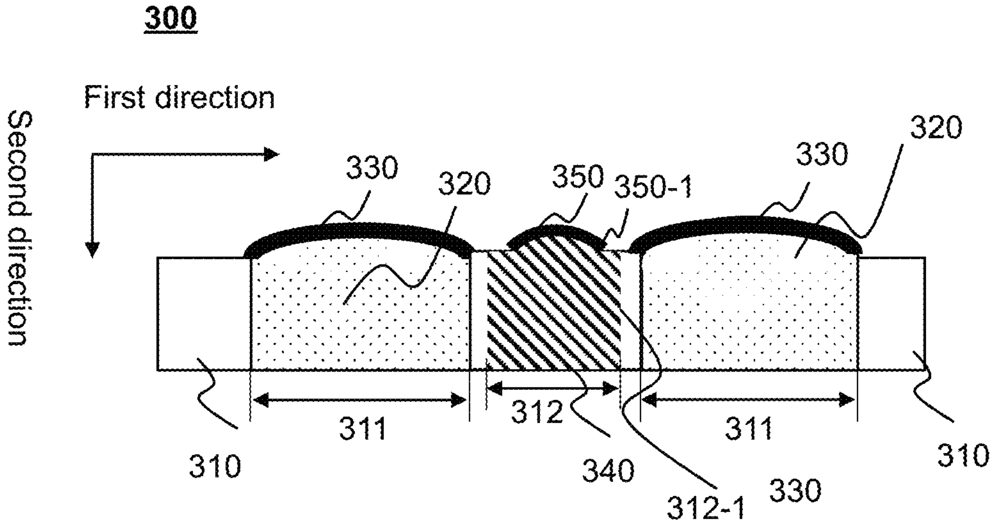
FIG. 4B is a schematic diagram illustrating a cross-sectional view of an exemplary physiological signal acquisition device along a plane perpendicular to a third direction according to some embodiments of the present disclosure.

FIG. 4A is a schematic diagram illustrating a top view of an exemplary physiological signal acquisition device according to some embodiments of the present disclosure. FIG. 4B is a schematic diagram illustrating a cross-sectional view of an exemplary physiological signal acquisition device along a plane perpendicular to a third direction according to some embodiments of the present disclosure.

As shown in FIGS. 4A and 4B, the physiological signal acquisition device 300 may further include at least one second guide groove 312 arranged in a first direction. Each of the at least one second guide groove 312 may be positioned between two adjacent first guide grooves 311 of the at least two first guide grooves 311. In some embodiments, a second absorbent member 340 may be arranged in the at least one second guide groove 312.

The at least one second guide groove 312 may be a groove/grooves configured to accommodate the second absorbent member 340 and/or an insulating water-conducting layer 350.

The second absorbent member 340 may be a component within the at least one second guide groove 312 configured to absorb moisture. In some embodiments, the second absorbent member 340 may be positioned within the at least one second guide groove 312 to absorb moisture and further guide moisture flow along a second direction. In some embodiments, a material of the second absorbent member 340 may be the same as a material of the first absorbent members 320. For example, both the second absorbent member 340 and the first absorbent members 320 may be made of moisture-absorbing modified polyester fiber. In some embodiments, the material of the second absorbent member 340 may differ from the material of the first absorbent members 320. For example, compared to the first absorbent members 320, the second absorbent member 340 may be made of a material with stronger water absorption properties to ensure that moisture is primarily absorbed by the second absorbent member 340 within the at least one second guide groove 312.

Figure 5:
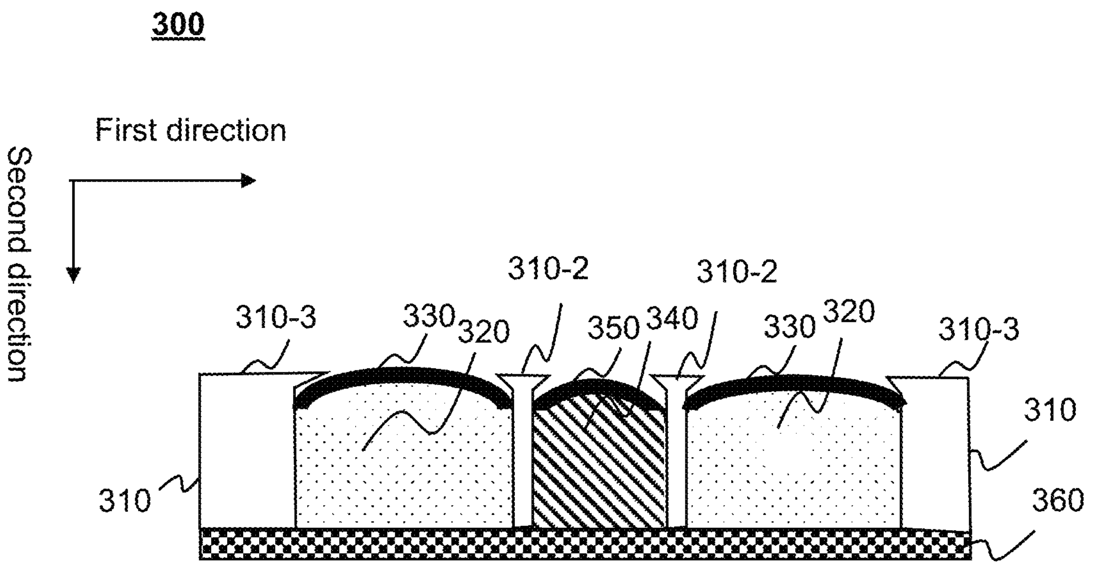
FIG. 5 is a schematic diagram illustrating a cross-sectional view of an exemplary physiological signal acquisition device along a plane perpendicular to a third direction according to some embodiments of the present disclosure.

In some embodiments, the physiological signal acquisition device may further include an insulating water-conducting layer 350. The insulating water-conducting layer 350 may be configured to guide moisture on a surface of the skin to a side away from the skin. In some embodiments, as shown in FIG. 4B, the insulating water-conducting layer 350 may cover the at least one second guide groove 312 and may be attached to a surface of the second absorbent member 340 near the skin. In some embodiments, the second absorbent member 340 in each second guide groove 312 may directly contact the insulating water-conducting layer 350. When the insulating water-conducting layer 350 contacts the skin, the second absorbent member 340 may provide a pressure to ensure close contact between the insulating water-conducting layer 350 and the skin. In some embodiments, the second absorbent member 340 may also have water absorption and moisture storage functions. After absorbing moisture (e.g., sweat from the surface of the skin), the moist second absorbent member 340 may provide moisture to the insulating water-conducting layer 350, ensuring good conductivity between the insulating water-conducting layer 350 and the skin, thereby improving the connection of the physiological signal acquisition device 300 with the skin. In some embodiments, to prevent excessive moisture stored in the second absorbent member 340 from forming a conductive path between at least two electrodes 330 on the surface of the skin, a side wall of each of the at least two first guide grooves 311 may be shaped in a certain manner (e.g., as shown in FIG. 5, a cross-section of the side wall of each of the at least two first guide grooves 311 perpendicular to a third direction is approximately Y-shaped). In some embodiments, the second absorbent member 340 may also have water absorption and quick-drying functions. When there is excess moisture, the second absorbent member 340 may absorb the moisture and facilitate evaporation of the moisture to prevent the formation of a conductive path between the at least two electrodes 330 due to excessive moisture.

In some embodiments, to ensure that all moisture absorbed by the insulating water-conducting layer 350 is guided into the at least one second guide groove 312, thereby preventing excessive moisture from forming a conductive path between at least two electrodes 330 on the surface of the skin, the insulating water-conducting layer 350 in each of the at least one second guide groove 312 may not contact the side wall of the second guide groove 312. For example, as shown in FIG. 4B, an endpoint 350-1 of the insulating water-conducting layer 350 in a second guide groove 312 does not contact a side wall 312-1 of the second guide groove 312. In other words, there may be a gap between the endpoint 350-1 of the insulating water-conducting layer 350 and the side wall 312-1 of the second guide groove 312 (e.g., the endpoint 350-1 of the insulating water-conducting layer 350 and the side wall 312-1 of the second guide groove 312 have a certain distance in the first direction), thereby allowing sweat produced by the skin to directly flow into the second absorbent member 340 through the gap.

FIG. 5 is a schematic diagram illustrating a cross-sectional view of an exemplary physiological signal acquisition device along a plane perpendicular to a third direction according to some embodiments of the present disclosure. In some embodiments, to prevent excessive moisture from forming a conductive path between at least two electrodes 330 on a surface of the skin, a side wall of each of the at least two first guide grooves 311 perpendicular to a third direction may be approximately Y-shaped. For example, as shown in FIG. 5, a side wall 310-2 and/or a side wall 310-3 of each of the at least two first guide grooves 311 perpendicular to the third direction are approximately Y-shaped, thereby allowing the physiological signal acquisition device 300 to form a wrapping-type containment chamber around the at least two electrodes 330 in contact with the surface of the skin, and preventing moisture from flowing along the first direction and forming a conductive path between the at least two electrodes 330.

In some embodiments, a bifurcated portion (e.g., an open end of the containment chamber) of the side wall 310-2 and/or the side wall 310-3 shaped approximately Y-shaped may be composed of an elastic material. For example, when the approximately Y-shaped bifurcated portion comes into contact with the skin and produce pressure, the bifurcated portion may undergo elastic deformation to relieve the pressure. In some embodiments, a material of the approximately Y-shaped bifurcated portion may be the same as a material of the first insulating membrane 310. In some embodiments, the approximately Y-shaped bifurcated portion may be integrally formed with the first insulating membrane 310.

In some embodiments, as shown in FIG. 5, the physiological signal acquisition device 300 further includes an isolation layer 360. In some embodiments, the isolation layer 360 may be positioned on a side of the physiological signal acquisition device 300 away from the skin. The isolation layer 360 may adhere to the first insulating membrane 310 to form the at least two first guide grooves 311 and/or the at least one second guide groove 312. In some embodiments, the isolation layer 360 may include an insulating membrane made of an insulating and waterproof material. For example, the isolation layer 360 may include a second insulating membrane. As another example, the isolation layer 360 may include modified fabric. In some embodiments, when the side (e.g., a piece of clothing containing the physiological signal acquisition device 300) of the physiological signal acquisition device 300 away from the skin becomes moistened, the isolation layer 360 may prevent the formation of a conductive path between the at least two electrodes 330 on the side away from the skin.

In some embodiments, the isolation layer 360 may include a second insulating membrane. For example, the second insulating membrane may be positioned on the side of the physiological signal acquisition device 300 away from the skin. The second insulating membrane may adhere to the first insulating membrane 310 to form the at least two first guide grooves 311 and/or the at least one second guide groove 312. In some embodiments, the first insulating membrane 310 and the second insulating membrane may be formed by a compression molding or may be integrally molded structures. In some embodiments, the first insulating membrane 310 and the second insulating membrane may be sewn together.

In some embodiments, a material of the second insulating membrane may be the same as or different from a material of the first insulating membrane 310. For example, the material of the second insulating membrane may include a polymer, and the material of the first insulating membrane 310 may include silicone. In some embodiments, both the material of the second insulating membrane and the material of the first insulating membrane 310 may include rubber. In some embodiments, to enhance breathability and flexibility of the physiological signal acquisition device 300, the second insulating membrane may be a grid structure. Each hole in the grid structure may extend along a second direction. In some embodiments, the second direction may be perpendicular to the surface of the skin (e.g., perpendicular to the first direction). For example, the grid structure of the second insulating membrane may include evenly distributed grids, with each grid extending along the second direction. The grid structure is breathable, and the flexibility is increased, thereby allowing moisture (e.g., sweat) to flow through along the second direction, and avoiding moisture flow along the first direction and preventing the formation of a conductive path between the at least two electrodes 330.

In some embodiments, the isolation layer 360 may include modified fabric to prevent absorbed moisture from conducting transversally in the first direction on the side of the physiological signal acquisition device 300 away from the skin. In some embodiments, the modified fabric may be insulating fabric, such as cotton, linen, synthetic fiber fabric, etc. In some embodiments, the modified fabric may be composite fabric.

Figure 6:
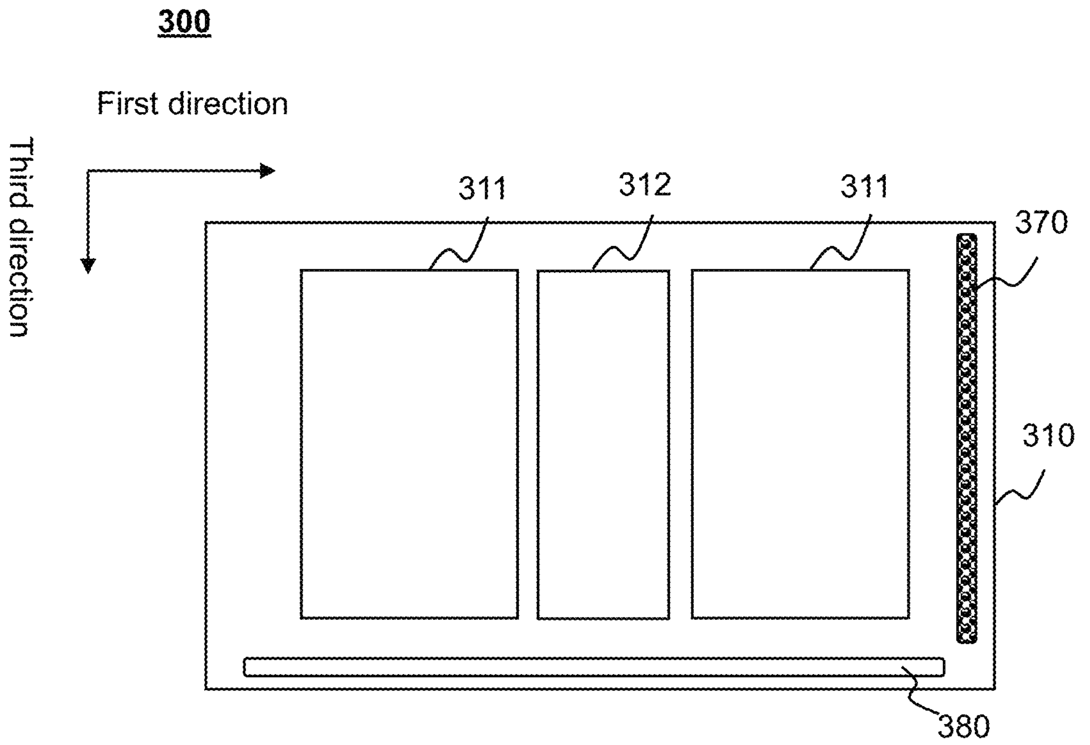
FIG. 6 is a schematic diagram illustrating a top view of an exemplary physiological signal acquisition device according to some embodiments of the present disclosure.

FIG. 6 is a schematic diagram illustrating a top view of an exemplary physiological signal acquisition device according to some embodiments of the present disclosure. In some embodiments, the physiological signal acquisition device 300 may further include an anti-skid strip 370 arranged on a first side of the physiological signal acquisition device 300. In some embodiments, as shown in FIG. 6, the first side may be a side of the physiological signal acquisition device 300 along a first direction. The anti-skid strip 370 may be configured to prevent slipping and prevent moisture from flowing in the first direction. In some embodiments, the anti-skid strip 370 may be a sealing strip, a sealing ring, an anti-skid tape, an anti-skid pad, or the like, or any combination thereof. In some embodiments, a material of the anti-skid strip 370 may have a high coefficient of friction. For example, the material of the anti-skid strip 370 may be rubber, or the like. FIG. 6 shows only one anti-skid strip 370, it should be understood that the physiological signal acquisition device 300 may include one or more anti-skid strips 370. For example, the physiological signal acquisition device 300 may include two anti-skid strips 370 located on two sides of the physiological signal acquisition device 300 along the first direction, thereby increasing stability during wearing and improving the accuracy of signal acquisition.

In some embodiments, the physiological signal acquisition device 300 may further include a channel 380 for conducting moisture. For example, the physiological signal acquisition device 300 may include a channel 380 arranged on a second side of the physiological signal acquisition device 300, and the channel 380 may be configured to guide the moisture to flow in the first direction. In some embodiments, the second side refers to a side of the physiological signal acquisition device along a third direction. A plane of the third direction and the first direction may be parallel to the surface of the skin in contact with the physiological signal acquisition device 300, and the third direction is perpendicular to the first direction. For example, in the case of a physiological signal acquisition device 300 for collecting electromyographic signals, the third direction may be perpendicular to an extension direction of the muscle fibers being measured. In some embodiments, the at least two electrodes 330 may be insulated from each other and insulated from the channel 380 to ensure that moisture flowing along the first direction through the channel 380 does not connect with the at least two electrodes 330, thereby avoiding the formation of a conductive path between the at least two electrodes 330 and speeding up the removal of moisture from the skin contact surface of the physiological signal acquisition device 300. FIG. 6 shows only one channel 380, however, it should be understood that the physiological signal acquisition device 300 may include two or more channels 380. For example, the physiological signal acquisition device 300 may include two channels 380 located on the two sides of the physiological signal acquisition device 300 along the third direction to accelerate the flow of moisture.

Some embodiments of the present disclosure also provide a wearable device comprising the physiological signal acquisition device 300 as described in any of the above embodiments. Exemplary wearable devices may include a wristband, a shoulder pad, an elbow pad, a knee pad, a piece of clothing, a pair of socks, or the like, or any combination thereof. In some embodiments, the physiological signal acquisition device 300 may be attached to the wearable device by adhesive, fasteners, Velcro, stitching, pressing, or other manners to facilitate the collection of physiological signals.

The beneficial effects of the embodiments of the present disclosure may include, but are not limited to: through the configuration of the structure and the selection of material for the physiological signal acquisition device, it becomes difficult for the at least two electrodes to conduct even in the presence of sweat or water infiltration, thereby improving the accuracy of physiological signal measurement by the physiological signal acquisition device.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure; Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures, or characteristics may be combined as suitable in one or more embodiments of the present disclosure;

Furthermore, it should be understood by those skilled in the art that various aspects of the present disclosure may be illustrated and described in several patentable forms or scenarios, including any new and useful process, machine, manufacture, or composition of matter, or any new and useful improvement thereof. Accordingly, aspects of the present disclosure may be implemented entirely in hardware, entirely in software (including firmware, resident software, microcode, etc.), or in a combination of hardware and software. The above hardware or software may be referred to as "data blocks," "modules," "engines," "units," "components," or "systems." Moreover, aspects of the present disclosure may be embodied as a computer product located on one or more computer-readable media, the product including computer-readable program code.

The computer storage medium may include a propagated data signal with computer-readable program code embedded thereon, such as in baseband or as part of a carrier wave. The propagated signal may take various forms, including electromagnetic, optical, or suitable combinations thereof. The computer storage medium may be any computer-readable medium other than a computer-readable storage medium that can communicate, propagate, or transport the program for use by or in connection with an instruction execution system, apparatus, or device. The program code on the computer storage medium may be transmitted using any appropriate medium, including wireless, wireline, optical fiber cable, RF, or any suitable combination of the foregoing.

The computer program code required to perform the operations of various parts of the present disclosure may be written in any combination of one or more programming languages, including object-oriented programming languages such as Java, Scala, Smalltalk, Eiffel, JADE, Emerald, C++, C#, VB.NET, Python, and conventional procedural programming languages such as C language, Visual Basic, Fortran 2003, Perl, COBOL 2002, PHP, ABAP, dynamic programming languages such as Python, Ruby, and Groovy, or other programming languages. The program code may run entirely on the user's computer, partly on the user's computer and partly on a remote computer, entirely on a remote computer or server, or as a standalone software package on the user's computer. In the latter scenario, the remote computer may be connected to the user's computer through any type of network, such as a local area network (LAN) or a wide area network (WAN), or connected to an external computer (e.g., via the Internet), or in a cloud computing environment, or provided as a service such as Software as a Service (Saas).

In addition, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, drawing, or description thereof for the purpose of streamlining the disclosure aiding in the understanding of one or more of the various inventive embodiments. This way of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the present disclosure are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameter set forth in the written description and attached claims are approximations that may vary depending upon the desired properties sought to be obtained by a particular embodiment. In some embodiments, the numerical parameter should be construed in light of the number of reported significant digits and by applying ordinary rounding techniques. Notwithstanding that the numerical ranges and parameter setting forth the broad scope of some embodiments of the present disclosure are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the present disclosure disclosed herein are illustrating of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A physiological signal acquisition device, comprising:

a first insulating membrane, wherein at least two first guide grooves are arranged in a first direction on the first insulating membrane, and the at least two first guide grooves are insulated from each other;

first absorbent members configured to absorb moisture, wherein the first absorbent members are arranged in the at least two first guide grooves;

at least two electrodes configured to contact a skin and acquire physiological signals, wherein the at least two electrodes cover the at least two first guide grooves and are attached to surfaces of the first absorbent members near the skin;

an insulating water-conducting layer configured to guide moisture on a surface of the skin to a side away from the skin; and at least one second guide groove arranged in the first direction, wherein each of the at least one second guide groove is positioned between two adjacent first guide grooves of the at least two first guide grooves, and a second absorbent member is arranged in the at least one second guide groove; and the insulating water-conducting layer covers the at least one second guide groove and is attached to a surface of the second absorbent member near the skin.

2. The physiological signal acquisition device of claim 1, wherein a material of the second absorbent member is the same as a material of the first absorbent members.

3. The physiological signal acquisition device of claim 1, wherein the insulating water-conducting layer in each of the at least one second guide groove does not contact a side wall of the second guide groove.

4. The physiological signal acquisition device of claim 1, wherein at least one side wall of each of the at least two first guide grooves includes a bifurcated portion, and the bifurcated portion is located at an end close to the surface of the skin.

5. The physiological signal acquisition device of claim 4, wherein the bifurcated portion enables the physiological signal acquisition device forms a containment chamber around the at least two electrodes in contact with the surface of the skin, and the bifurcated portion forms an open end of the containment chamber.

6. The physiological signal acquisition device of claim 1, wherein the first insulating membrane is a grid structure.

7. The physiological signal acquisition device of claim 1, further comprising a second insulating membrane, wherein the second insulating membrane is positioned on a side of the physiological signal acquisition device away from the skin.

8. The physiological signal acquisition device of claim 7, wherein the second insulating membrane is a grid structure.

9. The physiological signal acquisition device of claim 2, wherein a material of the first insulating membrane or a material of the second insulating membrane includes at least one of rubber, polymer, or silicone.

10. The physiological signal acquisition device of claim 1, further comprising modified fabric configured to prevent absorbed moisture from conducting transversally in the first direction, wherein the modified fabric is positioned on a side of the physiological signal acquisition device away from the skin.

11. The physiological signal acquisition device of claim 1, wherein the at least two electrodes include conductive fabric electrodes, and the at least two electrodes allow the moisture to penetrate and be absorbed by the first absorbent members.

12. The physiological signal acquisition device of claim 1, wherein a material of the first absorbent members includes sponge or quick-drying material.

13. The physiological signal acquisition device of claim 1, wherein the first direction is configured to be parallel to a surface of the skin.

14. The physiological signal acquisition device of claim 1, further comprising an anti-slip strip extends along a third direction and is arranged on a first side edge of the physiological signal acquisition device along the first direction, and the anti-slip strip is configured to prevent slipping and prevent the moisture from flowing in the first direction.

15. The physiological signal acquisition device of claim 14, further comprising a channel extending along the third direction and arranged on a second side edge of the physiological signal acquisition device along the third direction, and the channel is configured to guide the moisture to flow in the first direction.

16. The physiological signal acquisition device of claim 15, further comprising two channels located on two sides of the physiological signal acquisition device along the third direction.

17. The physiological signal acquisition device of claim 1, wherein a thickness of the first insulating membrane located between any two adjacent electrodes among the at least two electrodes is greater than or equal to a sum of a thickness of an electrode and a thickness of a first absorbent member in each of the at least two first guide grooves, and the thickness of the first insulating membrane refers to a length of the first insulating membrane in the second direction, the thickness of the electrode refers to a length of the electrode in the second direction, and the thickness of the first absorbent member refers to a length of the first absorbent members in the second direction.

18. The physiological signal acquisition device of claim 1, wherein when the physiological signal acquisition device is configured to collect EMG signals, the first direction is an extension direction of measured muscle fibers, and the third direction is perpendicular to the extension direction of the measured muscle fibers.

19. The physiological signal acquisition device of claim 1, wherein the at least one second guide groove is at least one groove configured to accommodate the second absorbent member and/or the insulating water-conducting layer.

20. A wearable device, comprising a physiological signal acquisition device, wherein the physiological signal acquisition device includes:

- a first insulating membrane, wherein at least two first guide grooves are arranged in a first direction on the first insulating membrane, and the at least two first guide grooves are insulated from each other;
- first absorbent members configured to absorb moisture, wherein the first absorbent members are arranged in the at least two first guide grooves;
- at least two electrodes configured to contact a skin and acquire physiological signals, wherein the at least two electrodes cover the at least two first guide grooves and are attached to surfaces of the first absorbent members near the skin; and
- an insulating water-conducting layer configured to guide moisture on a surface of the skin to a side away from the skin; and
- at least one second guide groove arranged in the first direction, wherein
  - each of the at least one second guide groove is positioned between two adjacent first guide grooves of the at least two first guide grooves, and a second absorbent member is arranged in the at least one second guide groove; and
  - the insulating water-conducting layer covers the at least one second guide groove and is attached to a surface of the second absorbent member near the skin.

* * * * *